United States Patent [19]

Rudy et al.

[11] Patent Number: 4,606,912

[45] Date of Patent: Aug. 19, 1986

[54] METHOD OF MAKING A CLEAR, STABLE AQUEOUS MOUTHWASH SOLUTION AND THE SOLUTION MADE BY THAT METHOD FOR THE ENHANCEMENT OF CELLS OF THE ORAL CAVITY AND THE REMINERALIZATION OF TEETH

[75] Inventors: Michael A. Rudy, Rochester, N.Y.; Vincent F. Lisanti, North Bergen, N.J.

[73] Assignee: Caries Research Group of Rochester, Inc., Rochester, N.Y.

[21] Appl. No.: 415,970

[22] Filed: Sep. 8, 1982

Related U.S. Application Data

[63] Continuation-in-part of Ser. No. 286,107, Jul. 22, 1981, abandoned.

[51] Int. Cl.$^4$ .......... A61K 7/16; A61K 7/18; A61K 7/22; A61K 33/16
[52] U.S. Cl. .................. 424/52; 424/57; 424/54; 424/151
[58] Field of Search .................. 424/49, 52

[56] References Cited

U.S. PATENT DOCUMENTS

| | | | |
|---|---|---|---|
| 2,975,102 | 3/1961 | Matsumura et al. | 424/54 |
| 3,330,732 | 7/1967 | Muhler | 424/49 |
| 3,378,445 | 4/1968 | Muhler | 424/49 |
| 3,452,049 | 6/1969 | Globus | 424/54 |
| 3,666,855 | 5/1972 | Muhler | 424/52 |
| 3,897,548 | 7/1975 | Katz | 424/54 |
| 3,975,514 | 8/1976 | Weisz | 424/52 |
| 3,988,434 | 10/1976 | Schole et al. | 424/54 |
| 4,024,237 | 5/1977 | Eichel et al. | 424/49 |
| 4,078,053 | 3/1978 | DePaula | 424/52 |
| 4,080,440 | 3/1978 | Diguilo et al. | 424/52 |
| 4,083,955 | 4/1978 | Grabenstetter et al. | 424/52 |
| 4,097,588 | 6/1978 | Levine | 424/52 |
| 4,108,980 | 8/1978 | Duff | 424/52 |
| 4,172,128 | 10/1979 | Thiele et al. | 424/95 |
| 4,177,258 | 12/1979 | Gappar et al. | 424/52 |
| 4,183,915 | 1/1980 | Gappar et al. | 424/52 |
| 4,224,310 | 9/1980 | Shah | 424/52 |
| 4,283,385 | 8/1981 | Dhabhar et al. | 424/52 |
| 4,357,318 | 11/1982 | Shah et al. | 424/52 |

FOREIGN PATENT DOCUMENTS 490384  2/1937  United Kingdom .................. 424/54

*Primary Examiner*—Shep K. Rose
*Attorney, Agent, or Firm*—Martin LuKacher

[57] ABSTRACT

A solutions for optimizing the environmental conditions within the human oral cavity is disclosed which enhances the functioning of cells of the oral cavity and promotes remineralization of teeth. These solutions are effective in treating and preventing caries and periodontal disease and reducing mouth odor and are easily and safely used by the lay population. A method of making the solutions which totally prevents the formation of calcium phosphate crystals, for example hydroxyapatite, is disclosed.

17 Claims, No Drawings

METHOD OF MAKING A CLEAR, STABLE AQUEOUS MOUTHWASH SOLUTION AND THE SOLUTION MADE BY THAT METHOD FOR THE ENHANCEMENT OF CELLS OF THE ORAL CAVITY AND THE REMINERALIZATION OF TEETH

This application is a continuation-in-part of application Ser. No. 286,107 filed July 22, 1981, now abandoned.

BACKGROUND OF THE INVENTION

This invention relates to a method for making a solution containing a composition for optimizing the environmental conditions within the human oral cavity and more particularly to a clear, stable aqueous solution containing a composition for remineralizing teeth and for improving the function of the oral leucocytes and to a method of preparing the same.

It has been heretofore known to utilize various solutions to aid in remineralizing teeth that have caries lesions in them and to enhance mineralization of normal teeth so they are much less likely to get caries. Because of the presence of calcium ions and phosphate ions in these solutions and the affinity of these ions for each other with the accompanying precipitation of calcium phosphate salt from solution, it is necessary to maintain these materials in separate containers until shortly prior to use. This requirement substantially renders the concept impractical as an item for consumer sales because it necessitates mixing proportionate amounts of each ingredient immediately prior to use. The public generally avoids products having this type of requirement. (See "Continuing Evaluation of the Use of Fluorides" AAAS Selected Symposium 11, Published by Westview Press, Inc., 5500 Central Ave., Boulder, Colo. 80301.)

U.S. Pat. No. 4,024,237, discloses chemical formulations (four illustrative formulations are included) which are comprised of non-toxic ingredients which favor and promote oral leucocyte function, including locomotion, phagocytosis and protoplasmic function resulting in the control and kill of bacteria (col. 3, lines 12–16). It is proposed that oral diseases such as periodontal disease and perhaps dental caries can be controlled and treated, especially early periodontal disease (col. 3, lines 16–21). The compositions of this patent contain non-toxic ingredients for four principal purposes:

(1) Maintaining a colloidal and viscous environment within the oral cavity which favors and promotes oral leucocyte locomotion, phagocytosis, and bacterial kill.

(2) Providing the oral leucocytes with a suitable source of energy when needed.

(3) Providing and maintaining a balanced ionic environment which favors and promotes locomotion, phagocytosis, and bacterial kill.

(4) Maintaining substantially a physiological pH in order to promote leucocyte functions while avoiding other tissue and cell injury (col. 3, lines 23–25).

The patent contains descriptions of studies which show that use produced increased numbers of healthy oral leucocytes which can be harvested, enhanced the number of oral leucocytes which showed bacterial killing ability, and produced a dramatic improvement of a periodontal disease (gingivitis) in subjects who used a formulation of the patent applied by themselves (col. 7 to col. 11, line 56).

U.S. Pat. No. 4,283,385 discloses dentrifrice preparations having incorporated therein ethylenediamine tetraacetic acid and the sodium salts thereof. Also employed in the dentrifrice are abrasives such as calcium carbonate and various calcium phosphates. These are employed generally in amounts of from about 5% to about 60% by weight. The minor amount of ethylenediamine tetracetic acid brings about the inhibition of the inactivation of soluble fluoride by the calcium containing abrasives.

U.S. Pat. Nos. 4,183,915 and 4,177,258 disclose a stable aqueous remineralizing solution having a source of calcium ions and phosphate ions sufficient to effect remineralization, a fluoride providing agent and a phosphorous containing antinucleating agent which absorbs onto a spherical nucleated particle of hydroxyapatite as it forms and entirely blocks crystal growth. The stable remineralizing solution is prepared by adding the calcium ion and phosphate ion sources to water and lowering the pH to keep the solution clear.

An article by Meyer and Nancollas entitled "The Influence of Multi-Dentate Organo-Phosphonates on the Crystal Growth of Hydroxyapatite." *Calc. Tiss. Res.*, 13:295–303 discusses the rate of crystal growth of hydroxyapatite seed crystals in stable supersaturated solutions of calcium phosphate in the presence of organic phosphorates. The most effective of the phosphorates, N, N, $N^1$, $N^1$ethylenediamine-tetra (methyline phosphonic acid) is structurally similar to ethylenediamine tetraacetic acid and would also be expected to be a good chelating agent for calcium ions situated at crystal surfaces.

It is an important consideration when dealing with prophylactic and therapeutic compositions for treatment of the human oral cavity, that users of these compositions can apply them at their own convenience without an appreciable amount of preparatory effort or the supervision of medically trained personnel. Further, the composition must be non-toxic in substantially all amounts if the objective is to make these compositions freely available to the general public.

It is therefore an object of this invention to provide an improved a method of preparing a solution containing a composition capable of being stored in a single container, for optimizing the environmental conditions within the human oral cavity and the solution made by a said method.

It is another object of this invention to provide an improved mouthwash solution and a method of preparing said solution maintainable as a one bottle solution capable of remineralizing caries lesions in the teeth and mineralizing normal teeth to prevent caries from forming.

It is a further object of this invention to provide an improved solution and a method of preparing said Composition maintainable as a one bottle solution to stimulate the white cells present in the oral cavity to act as a protective mechanism to prevent periodontal disease or treat it if already in existence.

It is still a further object of this invention to provide an improved a method of preparing said solution capable of achieving the advantages of both of the two previously stated objectives.

It is a still further object of this invention to provide an improved method of preparing an oral lavage solution which reduces or eliminates mouth odor.

SUMMARY OF THE INVENTION

The foregoing objects and others, which will become apparent from the following description are accomplished in accordance with the invention, generally speaking, by providing a method of making a clear aqueous mouthwash solution capable of remineralizing caries lesions in teeth by forming an aqueous solution containing a source of calcium ions and a chelating agent for calcium ions, causing the chelation of at least 50% of the calcium ions, and subsequently adding a source of phosphate ions to the aqueous solution. The invention also contemplates the composition prepared by the above stated process for remineralizing caries lesions and, in addition, for optimizing the environmental conditions within the human oral cavity.

DETAILED DESCRIPTION OF THE INVENTION

Thus, the invention contemplates a method of preparing the composition for remineralizing teeth; for enhancing the action of leucocytes or for accomplishing both of these functions. As a result of the promotion of the normal physiology and responses of the tissues and cells of the oral cavity, locally produced malodor is materially reduced or eliminated.

The method of the invention contemplates the steps of making a clear aqueous mouthwash solution by initially forming a solution in water of a source of calcium ions and a chelating agent for calcium ions wherein at least 50% of the calcium ions are chelated prior to the addition of a source (phosphate containing compound) of phosphate ions. By bringing about the chelation of at least 50% of the calcium ions, the precipitation of calcium phosphate (hydroxyapatite) from the solution is avoided. This invention contemplates the chelation of 100% of the calcium ions present in the solution. The percentage of calcium ions that are chelated can be controlled by controlling the ratio of the moles of chelating agent per mole of the calcium ion source. That is, for each mole of the calcium compound present in the aqueous solution as the source of calcium ions, 0.5 to 1.05 moles of chelating agent are used. The excess amount of chelating agent insures that all the calcium ions are chelated. While higher amounts of chelating agent can be employed, it is not necessary to do so from an economic viewpoint.

Subsequent to the chelation step, the phosphate containing compound and other desirable reagents such as fluoride containing and sodium containing compounds, in addition to others, which will become apparent hereinafter, may be added.

The chelating agent is one having an affinity for calcium and includes edetic acid (also known as EDTA, ethylenedinitrilo - tetraacetic acid, ethylene diamine tetraacetic acid), glyceric acid, tartaric acid, the sodium, potassium calcium and zinc salts of the above, and the like. As mentioned above, the chelating agent, or combination of chelating agents is employed in an amount such that at least 50% of the calcium ions are chelated thus preventing calcium phosphate salt from precipating from solution.

As examples of useful compounds as sources of calcium ions, mention may be made of calcium chloride, calcium carbonate, calcium fluoride, calcium chloride hexahydrate, calcium chloride dihydrate, and the like.

As examples of useful compounds as phosphate ion sources, mention may be made of monosodium dihydrogen phosphate, monosodium dihydrogen phosphate monohydrate, disodiummonohydrogen phosphate, monopotassium dihydrogen phosphate, and the like.

The remineralizing agent is made up of salts that will provide calcium (Ca) ions and phosphate (PO) ions and in addition fluoride (F) ions and sodium (Na) ions when in an aqueous solution.

An example of useful reagents that will contribute the necessary ions, mention may be made of calcium chloride, calcium fluoride, sodium fluoride, sodium chloride, disodiummonohydrogen phosphate, monopotassium dihydrogen phosphate and the like.

The salts are employed in amounts such that for each 100 parts of volume of aqueous solution, the required ions are present in the following (in parts by weight):

| | |
|---|---|
| Calcium | 0.005 to 0.09 |
| Phosphate | 0.005 to 0.09 |
| Fluoride | 0.001 to 0.01 |
| Sodium | 0.1 to 0.5 |

By "effective amount of remineralizing agent" is meant an amount when used in accordance with this invention which will bring about the remineralizing of teeth having caries lesions, or the mineralizing of normal teeth to prevent caries from forming by utilizing a mouthwash (lavage) having the various components in the amounts set forth above, this is achieved.

The leucocyte enhancing agent is a composition containing at least effective amounts of a non-toxic mixture of ingredients for: (1) maintaining a colloidal and viscous environment of the oral cavity which favors and promotes oral leucocyte locomotion, phagocytosis and bacterial kill; (2) providing the oral leucocytes with a suitable source of energy when needed; (3) providing and maintaining a balanced ionic environment which favors and promotes locomotion, phagocytosis and bacterial kill; and (4) maintaining the pH substantially the same as in the oral cavity, e.g., 5.5 to 9.0, but preferably as close to physiological pH as possible. The composition may, but not necessarily, also contain non-toxic ingredients for providing a negative charge potential in the oral cavity to reduce clustering of leucocytes and to eliminate agglutination and precipitation of protoplasmic particles.

As examples of useful reagents for maintaining the requisite colloidal and viscous environment, mention may be made of the dextrans, especially those having molecular weights ranging from between 15,000 to 40,000,000 Daltons, preferably those from about 60,000 to 90,000 Daltons; cellulose and hydroxyethyl cellulose; polyvinylpyrrolidone; gelatin, hydroxyethyl starch, etc.

As examples of energy-providing reagents, mention may be made of carbohydrates such as glucose, sucrose, and fructose; phosphorylated sugar intermediates such as glucose-6-phosphate, fructose-6-phosphate non-phosphorylated sugar intermediates such as salts, preferably alkali metal salts (e.g., sodium, potassium or lithium salts) of pyruvic, lactic, acetic acid, or citric acid, etc., and metabolizable fats and proteins.

As examples of useful reagents for providing a properly balanced ionic environment, mention may be made of inorganic salts such as sodium chloride, potassium chloride, calcium chloride, magnesium chloride; magnesium sulfate; monopotassium dihydrogen phosphate, monosodium dihydrogen phosphate, dipotassium monohydrogen phosphate, disodium monohydrogen phosphate; sodium bicarbonate, etc.

As examples of reagents for maintaining the pH within the desired range, mention may be made of phosphate buffers, $CO_2$-bicarbonate buffer, tris buffers, glycylglycine buffer, etc.; the $CO_2$-bicarbonate buffer being preferred.

As examples of useful ingredients for proving a negative charge potential, mention may be made of heparin, chrondroitin sulfate; and other polyanionic polysaccharides.

The effective amounts of the above mentioned four classes of ingredients may be readily determined empirically by those skilled in the art of sampling the formulation and then examining under the microscope leucocytes taken from the oral cavity to determine if they are viable, being capable of healthy protoplasmic flow, locomotion and phagocytosis and bacterial kill after application of the composition. By simple and routine analysis, necessary adjustments in the formulation may be made to achieve optimum results.

In such a manner, we have determined the preferred ranges of ingredients set forth in the following table, it being appreciated that beneficial results may also be obtained by employing lesser or greater amounts than those recited.

TABLE

| Ingredients | Parts by Weight per 100 Parts by Volume of Aqueous Solution |
|---|---|
| 1. | 0.50 to 10.0 |
| 2. | 0.10 to 3.0 |
| 3. | 0.26 to 5.2 |
| 4. | 0.015 to 1.5 |

The compositions in accordance with this invention may also contain therapeutic concentrations of zinc as zinc salts, such as, zinc chloride, zinc sulfate, zinc gluconate and the zinc salts of the chelating agents, mentioned above. Zinc has a stabilizing effect on the hydroxyapatible structure of the tooth, increasing hardness and decreasing solubility rendering the tooth more resistent to caries formation. Non-therapeutic reagents, which perform specifically desired functions may also be included, such as flavoring and/or effervescing ingredients, e.g. citric acid; preservatives, such as benzoic acid, paraamino-benzoic acid or their potassium or sodium salts; anti-oxidants, colorants, viscous reagents, solvents and the like.

For optimum effectiveness, the prophylactic compositions of this invention should be retained in solution in the oral cavity for at least thirty and preferably at least sixty seconds. Since the compositions are completely non-toxic, they need not be expectorated, but may be swallowed. This important aspect of the invention permits the prophylactic compositions to be employed at any time, e.g., in restaurants, or any other public place and/or while the individual is in transit. The mouthwash initiates action as soon as it is taken in the mouth.

For optimum effectiveness, treatment should be repeated at least upon arising, after eating, smoking, drinking high concentration alcoholic beverages, and before going to sleep. An important feature of the present invention is that the compositions are completely non-toxic, and hence, may be taken appreciably more often, if desired. It will be appreciated that lesser than optimum treatment will provide benefits accordingly.

The invention is further illustrated by the following examples in which all weights, specified in grams are per 100 cc of aqueous solution:

EXAMPLE 1

Mineralizing Solution with Chelating Agent

Preparation of 100 cc of mineralizing solution;

About 80 cc of distilled, deionized water is placed in a 150 cc beaker, and a magnetic stirring bar is placed in the beaker.

The pH is adjusted to 7.8 using sodium hydroxide (NaOH) and a pH meter.

About 0.175 gm edetic acid and about 0.05 gm NaOH are added to the beaker, and the solution is heated to approximately 60° C. and held at that temperature and stirred for 15 minutes. A clear solution results.

The solution is cooled to below 20°C. and the pH is adjusted to 8.0 using NaOH and a pH meter.

About 0.1192 gm calcium chloride hexahydrate ($CaCl_2$-$6H_2O$) is added and stirred, and NaOH is added with stirring until the solution has a pH of between 8 and 10.

The following chemicals are then added, with stirring, in sequence:
0.0011 gm NaF (Sodium fluoride)
0.5592 gm NaCl (sodium chloride)
0.056 gm $NaH_2PO_4.H_2O$ (monosodium dihydrogen phosphate monohydrate)

The pH is then adjusted to between 7.5 to 8.0, with 7.8 being optimum, with NaOH.

The volume is adjusted to 100 cc with distilled, deionized water.

The solution prepared by using the above 8 steps has remained clear for 6 months and held a pH of 7.79 for that time.

The aforementioned solution is the basic mineralizing solution. Larger volumes of the solution are produced simply by scaling up all the ingredients.

EXAMPLE 2

Mineralizing Solution with Chelating Agent and Oral Cell (leucocyte) Enhancing Agent This formulation process is expanded to produce the combined mineralizing solution and oral tissue enhancing solution. The previously described seven steps are repeated, and in addition, the following chemicals are added, with stirring, in sequence:
sodium bicarbonate—7.743 gm
potassium chloride—0.061 gm
magnesium sulfate .$7H_2O$—0.051 gm
D-glucose—1.695 gm
hydroxyethyl starch or dextran—2.0 to 8.50 gm The final volume is adjusted to 100 cc with distilled-deionized water, and the pH is adjusted to 7.5 to 8.0, with 7.8 being optimal, with NaOH.

EXAMPLE 3

Remineralizing Agent plus Chelating Agent

The procedure of Example 1 is repeated but instead of the reagents and quantities as used therein, the following are used:

| | |
|---|---|
| calcium chloride | 0.0654 gm |
| sodium fluoride | 0.0109 gm |
| disodiummonohydrogen phosphate | 0.0577 gm |
| edetic acid | 0.172 gm |

| -continued | |
|---|---|
| sodium chloride | 0.5592 gm |

EXAMPLE 4

Remineralizing Agent plus Chelating Agent

The procedure of Example 1 is repeated but instead of the reagents and quantities as used therein, the following are used:

| calcium chloride | 0.0654 gm |
|---|---|
| sodium fluoride | 0.0109 gm |
| disodiummonohydrogen phosphate | 0.0577 gm |
| glyceric acid | 0.0624 gm |
| sodium chloride | 0.5592 gm |

EXAMPLE 5

Remineralizing Agent plus Chelating Agent

The procedure of Example 1 is repeated but instead of the reagents and quantities as used therein, the following are used:

| calcium chloride | 0.0654 gm |
|---|---|
| sodium fluoride | 0.0109 gm |
| disodiummonohydrogen phosphate | 0.0577 gm |
| edetic acid | 0.086 gm |
| glyceric acid | 0.0312 gm |
| sodium chloride | 0.5592 gm |

EXAMPLE 6

Remineralizing Agent plus Leucocyte Enhancing Agent plus Chelating Agent

The procedure of Example 2 is repeated but instead of the reagents and quantities as used therein, the following are used:

| calcium chloride | 0.047 gm |
|---|---|
| sodium chloride | 2.373 gm |
| sodium fluoride | 0.010 gm |
| monopotassium dihydrogen phosphate | 0.029 gm |
| dextran | 8.500 gm |
| D-glucose | 1.695 gm |
| sodium bicarbonate | 7.743 gm |
| potassium chloride | 0.061 gm |
| magnesium sulfate 7H$_2$O | 0.051 gm |
| edetic acid | 0.124 gm |

EXAMPLE 7

Remineralizing Agent plus Leucocyte Enhancing Agent plus Chelating Agent

The procedure of Example 2 is repeated but instead of the reagents and quantities as used therein, the following are used:

| calcium chloride | 0.047 gm |
|---|---|
| sodium chloride | 2.373 gm |
| sodium fluoride | 0.010 gm |
| monopotassium dihydrogen phosphate | 0.029 gm |
| dextran | 8.500 gm |
| D-glucose | 1.695 gm |
| sodium bicarbonate | 7.743 gm |
| potassium chloride | 0.061 gm |

| -continued | |
|---|---|
| magnesium sulfate 7H$_2$O | 0.051 gm |
| glyceric acid | 0.045 gm |

EXAMPLE 8

Remineralizing Agent plus Leucocyte Enhancing Agent plus Chelating Agent

The procedure of Example 2 is repeated but instead of the reagents and quantities as used therein, the following are used:

| calcium chloride | 0.047 gm |
|---|---|
| sodium chloride | 2.373 gm |
| sodium fluoride | 0.010 gm |
| monopotassium dihydrogen phosphate | 0.029 gm |
| dextran | 8.500 gm |
| D-glucose | 1.695 gm |
| sodium bicarbonate | 7.743 gm |
| potassium chloride | 0.061 gm |
| magnesium sulfate 7H$_2$O | 0.051 gm |
| edetic acid | 0.062 gm |
| glyceric acid | 0.023 gm |

The systematic use of a mouthwash in accordance with the above examples results in the establishment of an improved environment within the human oral cavity resulting in the remineralizing of teeth and improved function of oral leucocytes, aiding in the preservation of cellular and tissue elements therein, together with the prevention of periodontal disease and dental caries, and the reduction or elimination of mouth odor.

We claim:

1. A method of making a clear, stable, aqueous mouthwash solution capable of remineralizing caries lesions in teeth which comprises forming a stable, aqueous solution containing a source of calcium ions in an amount therapeutically effective to produce said remineralizing of caries lesions in teeth and a chelating agent for calcium ions, causing the chelation of at least 50% of the calcium ions by preparing a clear, aqueous solution of the chelating agent having an alkaline pH, then adding the source of calcium to said clear, aqueous solution of the chelating agent, and then adjusting the pH to an alkaline pH, and subsequently adding a source of phosphate ions to said aqueous solution.

2. The method of claim 1 wherein from 50 to 100 percent of the calcium ions are chelated.

3. The method of claim 2 wherein 100% of the calcium ions are chelated.

4. The method of claim 1 wherein the chelating agent is selected from the group consisting of edetic acid, glyceric acid, tartaric acid and the sodium potassium calcium and zinc salts thereof.

5. The method of claim 4 wherein the group member is edetic acid.

6. The method of claim 1 wherein from about 0.5 mole to about 1.05 mole of chelating agent is present in the aqueous solution per mole of the source of calcium ions present.

7. The method of claim 1 wherein a molar excess of chelating agent is present in the aqueous solution with respect to the source of calcium ions present.

8. The method of claim 1 wherein, subsequent to the addition of the source of phosphate ions to the aqueous solution, a leucocyte enhancing agent is added.

9. The method of claim 1 wherein subsequent to the step of causing the chelation of calcium ions, a source of fluoride ions is added to the aqueous solution.

10. The method of claim 1 wherein the pH of the final aqueous solution is adjusted to from 7.8 to 8.

11. The method of claim 8 wherein the leucocyte enhancing agent is a non-toxic mixture of effective amounts of: (1) at least one compound selected from the group consisting of dextran, cellulose ethers, polyvinylpyrrolidone and gelatin for maintaining a colloidal and viscous environment within the oral cavity which favors and promotes oral leucocyte locomotion, phagocytosis and bacterial kill; (2) at least one compound selected from the group consisting of carbohydrates, fats and proteins to provide a source of energy for said oral leucocytes; (3) an inorganic salt providing and maintaining a balanced ionic environment which favors and promotes locomotion, phagocytosis and bacterial kill; and (4) at least one compound selected from the group consisting of phosphate buffers, carbon dioxide-bicarbonate buffers, tris buffers and glycylglycine buffers for maintaining substantially a physiological pH to promote leucocyte functions while avoiding other tissue and cell injury.

12. A clear aqueous mouthwash solution capable of remineralizing caries lesions in teeth prepared by the process of claim 1.

13. The mouthwash solution as set forth in claim 12 to which a leucocyte enhancing agent is added.

14. The mouthwash solution as set forth in claim 12 to which a source of flouride ions is added.

15. The mouthwash solution as set forth in claim 13 wherein the leucocyte enhancing agent is a non-toxic mixture of effective amounts of: (1) at least one compound selected from the group consisting of dextran, cellulose ethers, polyvinylpyrrolidone and gelatin for maintaining a colloidal and viscous environment within the oral cavity which favors and promotes oral leucocyte locomotion, phagocytosis and bacterial kill; (2) at least one compound selected from the group consisting of carbohydrates, fats and proteins to provide a source of energy for said oral leucocytes; (3) an inorganic salt providing and maintaining a balanced ionic environment which favors and promotes locomotion, phagocytosis and bacterial kill; and (4) at least one compound selected from the group consisting of phosphate buffers, carbon dioxide-bicarbonate buffers, tris buffers and glycylglycine buffers for maintaining substantially a physiological pH to promote leucocyte functions while avoiding other tissue and cell injury.

16. The method according to claim 1 wherein said alkaline pH of said clear, aqueous solution of said chelating agent is at least 7.8.

17. The method according to claim 16 wherein the pH of said clear, acqueous solution of said chelating agent to which said calcium source is added is adjusted between 8 and 10.

* * * * *